(12) United States Patent
Hargett, Jr. et al.

(10) Patent No.: US 6,927,371 B1
(45) Date of Patent: *Aug. 9, 2005

(54) PRESSURE VESSEL WITH COMPOSITE SLEEVE

(75) Inventors: Wyatt Price Hargett, Jr., Matthews, NC (US); Edward Earl King, Charlotte, NC (US)

(73) Assignee: CEM, Inc., Matthews, NC (US)

( * ) Notice: Subject to any disclaimer, the term of this patent is extended or adjusted under 35 U.S.C. 154(b) by 150 days.

This patent is subject to a terminal disclaimer.

(21) Appl. No.: 09/668,811

(22) Filed: Sep. 23, 2000

Related U.S. Application Data

(62) Division of application No. 09/260,209, filed on Mar. 1, 1999, now Pat. No. 6,534,140.

(51) Int. Cl.[7] .................................. B65D 6/34
(52) U.S. Cl. ............... 219/679; 220/62.19; 422/102
(58) Field of Search ................ 220/23.91, 240, 220/801, 62.22, 646, 647, 648, 62.19, 581; 422/242, 102; 219/679

(56) References Cited

U.S. PATENT DOCUMENTS

| | | | |
|---|---|---|---|
| 3,368,708 A | | 2/1968 | Pflederer |
| 3,426,940 A | * | 2/1969 | Broeman .................... 220/644 |
| 4,248,831 A | | 2/1981 | Hughes |
| 4,517,895 A | | 5/1985 | Rucker |
| 4,882,128 A | * | 11/1989 | Hukvari et al. ............. 422/119 |
| 4,933,529 A | * | 6/1990 | Saville ....................... 219/686 |
| 5,230,865 A | | 7/1993 | Hargett et al. |
| 5,236,669 A | * | 8/1993 | Simmons et al. ........... 422/113 |
| 5,270,010 A | * | 12/1993 | Lautenschlager ........... 422/102 |
| 5,369,034 A | | 11/1994 | Hargett et al. |
| 5,427,741 A | | 6/1995 | Bennett |
| 5,520,886 A | | 5/1996 | Bennett et al. |
| 5,556,673 A | | 9/1996 | Giraud |
| 6,005,191 A | | 12/1999 | Tzeng et al. |
| 6,136,273 A | * | 10/2000 | Seguin et al. ........... 220/801 X |
| 6,136,276 A | * | 10/2000 | Hargett et al. ............. 422/102 |
| 6,145,693 A | * | 11/2000 | Berglund .................... 220/589 |
| 6,177,054 B1 | * | 1/2001 | Bartels ....................... 422/240 |
| 6,189,723 B1 | * | 2/2001 | Davis et al. ................ 220/586 |
| 6,287,526 B1 | * | 9/2001 | Hargett, Jr. ................ 422/242 |
| 6,534,140 B2 | * | 3/2003 | Hargett, Jr. et al. ....... 428/36.2 |
| 2002/0176954 A1 | * | 11/2002 | Hargett et al. ............ 428/36.3 |

FOREIGN PATENT DOCUMENTS

| | | |
|---|---|---|
| DE | G9311661.6 U | 12/1993 |
| DE | 9309355 U | 11/1994 |
| EP | 0628344 A1 | 12/1994 |

* cited by examiner

Primary Examiner—Joseph C. Merek
(74) Attorney, Agent, or Firm—Summa & Allan, P.A.

(57) ABSTRACT

The vessel assembly includes a polymeric cylinder and a circular polymeric cap for the cylinder, the cylinder being closed at one end and open at the other end to receive the cap. The open end of the cylinder has a lip that is beveled inwardly from the open end, and the circular polymeric cap has a beveled lower edge that engages the beveled lip when the cap is place upon the polymeric cylinder. For high pressure applications, a choke cylinder depends from the beveled lower edge of the cap, and has an outer diameter substantially the same as the inner diameter of the polymeric cylinder so that the choke provides a self sealing mechanism for the cylinder as pressure from a chemical reaction increases within the cylinder. A composite sleeve surrounds the polymeric cylinder, and includes at least one wound fabric layer in which the winding can be a filament or a yarn.

10 Claims, 2 Drawing Sheets

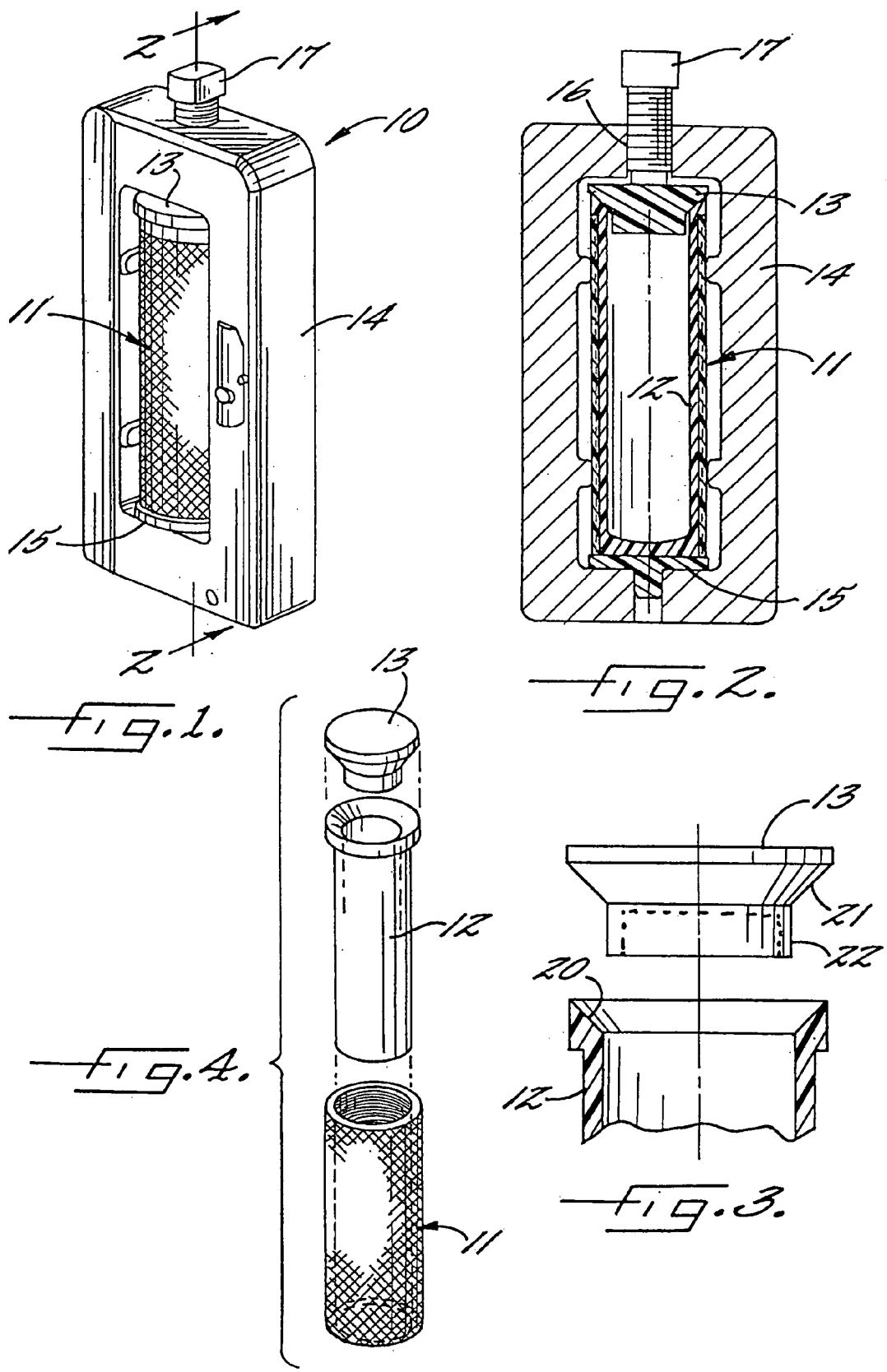

PRESSURE VESSEL WITH COMPOSITE SLEEVE

CROSS-REFERENCE TO RELATED APPLICATION

This application is a divisional of U.S. application Ser. No. 09/260,209, filed Mar. 1, 1999, now U.S. Pat. No. 6,534,140.

FIELD OF THE INVENTION

The present invention relates to microwave assisted chemistry, and in particular relates to a reaction vessel structure that can withstand high pressures without catastrophic failure.

BACKGROUND OF THE INVENTION

Microwave assisted chemistry refers to the use of microwaves to initiate or accelerate chemical reactions. Microwave assisted chemistry is particularly useful in heating materials that are responsive to microwave radiation because under most circumstances, the resulting heating takes place much more rapidly than it would if the reactions were initiated or accelerated using more conventional heating techniques such as convection or conduction heating.

Microwave assisted chemistry can be used in a variety of chemical processes including moisture determination, ashing, digestion, extraction, and others. Under some circumstances, these various techniques are preferably or necessarily carried out in sealed vessels which, because of the generation or expansion of gases inside, must be able to withstand high pressures.

Accordingly, a number of pressure vessels have been developed that are suitable for high-pressure microwave assisted chemistry. Such vessels are typically formed of microwave transparent materials that offer the structural capabilities required to withstand such high pressures. High-strength polymers are exemplary of such materials and offer the required microwave transparency and resistance to chemical attack. Such materials tend to be brittle, however, so that failure under pressure tends to destroy the vessel quickly and release its contents suddenly.

One recent advance in the construction of such vessels has been to use a composite sleeve as one of the outer portions of the reaction vessel. The composite is formed of several alternating layers of plastic (polymer) and fabric. In such a composite structure, the materials synergistically complement each other by providing characteristics unavailable from the other material, and by providing a structure with characteristics better than either material alone In the case of sleeves for microwave vessels, the plastic portions of such a vessel offer chemical resistance and structural strength. The fabric portions offer additional strength as well as flexibility and the ability to change shape without breaking or shattering. Accordingly, when plastic-fabric composite vessels fail under pressure, they tend to fail rather gently. Stated differently, a fabric vessel, even if it could be constructed to hold gases, would never offer the strength required for high-pressure conditions. Alternatively, engineering resins and other materials can withstand high pressures, but tend to fail by shattering. When used together in a composite structure, however, the combination provides the strength for maintaining a high pressure in the vessel, while preventing shattering should the plastic fail.

Versions of such composite fabric vessels are disclosed, for example, in U.S. Pat. Nos. 5,427,741 and 5,520,886, both of which are commonly assigned with the present invention. Another version is set forth in co-pending and commonly assigned application Ser. No. 09/062,858, filed Apr. 20, 1998, the contents of which are incorporated entirely herein by reference ("the '858 application").

As composite pressure vessels have become more widely used because of their advantages, certain characteristics have become more evident that can be improved upon. In particular, and taking for example the vessel structure illustrated in the co-pending '858 application, the flexible nature of the woven fabric layers tends to be such that if the vessel is exposed to high pressure, it may distort slightly. The vessel's characteristics are such that it will stay distorted even after the pressure is removed or released. By "distorted," it will be understood that only a very slight change of shape may have taken place, sometimes as little as 0.001 inch. Nevertheless, when dealing with gases, such a change in dimension is enough to prevent the vessel from maintaining an effective seal under high pressure.

Additionally, in the vessel illustrated in the '858 application, the lid for the reaction portion of the vessel is sealed to the top of the vessel using a flat surface-flat surface contact arrangement (e.g., FIGS. 2 and 4 thereof). As in the case of slight flexing of the composite sleeve, slight deviations from the flat-on-flat contact can allow gases to escape. In some cases such self-venting is desirable and helps keep a reaction at or within desired pressure limits. In other cases, however, unintended venting can release gases (including reagents) and prevent the intended reaction from taking place.

Accordingly, a need exists for pressure vessels that incorporate the advantages of protective composite sleeves, but that improve upon the characteristics of the present vessels and reduce the possibility for distortion or leakage.

OBJECT AND SUMMARY OF THE INVENTION

Therefore, it is an object of the present invention to provide an improved vessel for high-pressure microwave assisted chemistry that takes advantage of the characteristics of composite materials and yet improves upon the existing structures.

The invention meets this object with a protective composite sleeve for a microwave transparent vessel. The sleeve comprises a microwave transparent inner cylindrical polymeric layer, a first microwave transparent wound layer adjacent to and concentric with the inner polymeric layer, and in which the winding is selected from the group consisting of filaments and yarns. A microwave transparent outer polymeric layer completes the basic sleeve structure.

In another aspect, the invention comprises the composite material from which the sleeve is made.

In yet another aspect, the invention comprises a pressure vessel assembly for microwave assisted chemistry that incorporates the composite sleeve.

These and other objects of the invention and the manner in which they are accomplished will be more clearly understood when taken in conjunction with the detailed description and the accompanying drawings in which:

BRIEF DESCRIPTION OF THE DRAWINGS

FIG. 1 is a perspective view of an embodiment of a pressure vessel for microwave assisted chemistry according to the present invention;

FIG. 2 is a cross-sectional view of the vessel and its frame taken along lines 2—2 of FIG. 1;

FIG. 3 is an enlarged exploded partial view of the inner liner and lid portions of the vessel according to the present invention;

FIG. 4 is an exploded perspective view of the composite sleeve according to the present invention, the vessel liner, and its lid;

DETAILED DESCRIPTION

Figure 5:
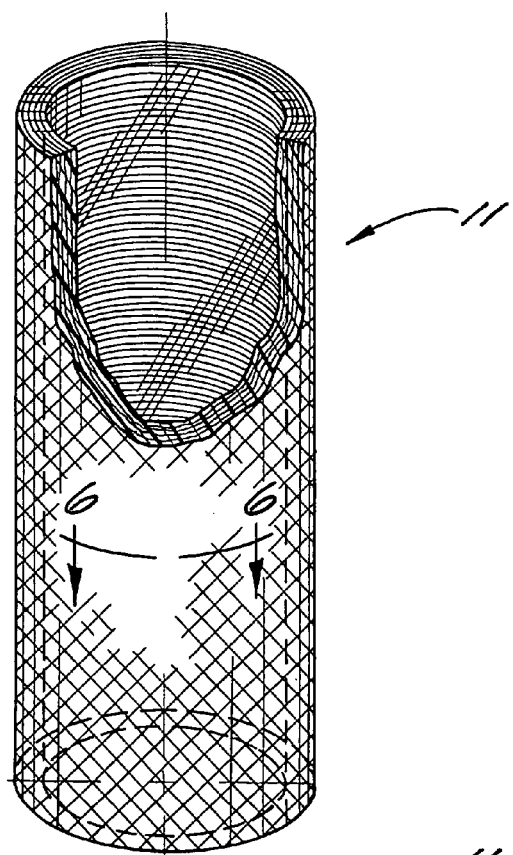
FIG. 5 is a partially cut-away perspective view of a composite sleeve according to the present invention.

The present invention is a self-sealing vessel assembly for high-pressure microwave assisted chemistry that is illustrated in perspective view at 10 in FIG. 1. The vessel assembly 10 includes a protective composite sleeve 11 that is also illustrated in more detail in FIGS. 4, 5, and 6. The sleeve surrounds a microwave transparent polymeric reaction cylinder 12 (e.g., FIGS. 3 and 4) and a circular polymeric cap 13 for the cylinder 12. It will be understood that although the invention herein is described in terms of cylindrical vessels and sleeves, and that such are typically most preferred and convenient for manufacture and use, other shapes such as polygons could be used provided they otherwise offer the structural integrity of a cylinder.

The vessel assembly 10 further includes a frame 14 into which the composite sleeve 11, the reaction cylinder 12, and the cap 13 fit along with a structural support disc 15 that is included for strength purposes so that the reaction cylinder 12 can be tailored for chemical inertness rather than strength. The frame 14 includes a threaded opening 16 (FIG. 2) that receives a bolt 17 that can be tightened down against the cap 13. In use, the bolt 17 helps secure the cap 13 at lower pressures while the cap itself helps secure the opening with a self-sealing mechanism at higher pressures as will be explained in more detail herein. For higher pressure operation, the cap 13 and bolt 17 are often used in combination with a structural disk (not shown) that adds additional strength to the cap 13, the material for which is typically chosen for chemical resistance.

As set forth in the '858 application incorporated above, one purpose of the frame 14 is to maintain the vessel under seal at certain pressures, while allowing the vessel to vent (as the frame flexes) at other (higher) pressures. The design and materials for the frame are accordingly selected for this purpose.

As illustrated in FIGS. 2, 3, and 4, the reaction cylinder 12 is closed at its lower end and open at the other end to receive the cap 13. The open end of the cylinder 12 comprises a lip 20 that is beveled inwardly from the open end and the cap 13 has a beveled lower edge 21 that engages the beveled lip 20 when the cap 13 is placed on the cylinder 12. In certain embodiments, the cap 13 further comprises a choke cylinder 22 that depends from the beveled lower edge 21. The choke cylinder 22 has an outer diameter substantially the same as the inner diameter of the polymeric cylinder 12 so that the choke 22 provides a self-sealing mechanism for the cylinder 12 as pressure from a microwave assisted chemical reaction increases within the cylinder 12. The use of the bolt 17 against the cap 13 together with the choke cylinder 22 keeps the reaction cylinder 12 sealed at both low and high pressures. The bolt 17 keeps the cap secured at lower pressures, while at higher pressures, the pressure exerted by a gas against the inner walls of the depending choke cylinder 22 urges them against the inner circumference of the reaction vessel 12 in a manner that seals the vessel quite efficiently at the intended pressures.

In other embodiments, and as set forth in the '858 application, the choke cylinder 22 is omitted. In these embodiments, the frame is designed to flex at certain pressures so that the cap 13 will briefly disengage from the vessel 12 at such pressures. In this manner the assembly releases pressure and then immediately re-seals itself as the frame returns to it original orientation against the vessel 12 and cap 13. As noted above, the structural design of the frame can be selected to determine the pressure at which the frame will allow the cap to open.

The reaction cylinder 12 and cap 13, along with all of the other materials in the vessel assembly 10, are formed of a microwave transparent materials, and in preferred embodiments, the reaction cylinder 12 and the cap 13 are formed of polymerized fluorinated hydrocarbons such as polytetrafluoroethylene, which is commonly available under the trade name TEFLON®.

Those familiar with polymers that are microwave transparent, chemically inert, and structurally appropriate will recognize that other polymers meeting these characteristics can be used for the vessel and cap and can be selected without undue experimentation. Exemplary fluoropolymers and other materials are also described in U.S. Pat. No. 5,520,886, at column 5, lines 17–55. The contents of Pat. No. 5,520,886 are incorporated entirely herein by reference.

As illustrated in FIGS. 1 and 2, the supporting frame 14 extends along the length of the reaction cylinder 12 and the composite sleeve 11 and then across the lid 13 as well as across the closed end of the cylinder for preventing the lid 13 from being displaced from the cylinder until the pressure generated inside the vessel reaches the desired release point.

The beveled lip 20 of the reaction cylinder and the beveled edge 21 of the cap 13 form a much more efficient seal in vessel systems of this type than do flat surfaces that simply bear against one another in planar fashion. The use of the beveled lip 20 and beveled edge 21 greatly increases the surface contact area between the lid 13 and the reaction cylinder 12 thus providing a more efficient seal under the various stresses that the overall vessel assembly experiences as gas pressure increases within the cylinder 12. Furthermore, the structural stability provided by the improved composite sleeve makes the beveled choke cap 13 much more effective than it would be otherwise, as well as increasing its durability.

In preferred embodiments, the composite sleeve 11 comprises a microwave transparent inner cylindrical polymeric layer 23, a first microwave transparent wound layer 24 adjacent to and concentric with the inner polymer layer 23 in which the winding (FIG. 5) is selected from the group consisting of filaments and yarns, and a microwave transparent outer polymeric layer 25.

It has been discovered, according to the present invention, that incorporating at least one (and possibly several) textile layers in which the filaments or yarns are wound rather than woven, knitted, or nonwoven, maintains the structural integrity of the sleeve 11 for many more cycles of operation than has been the case with composite sleeves in which the fabric layers have been, for example, woven. In particular, it has been discovered if the windings are made under tension, they form a particularly strong structural geometry that remains unaffected even under exposure to high pressure. This appears to result from the windings being directly circumferential to the radial forces inside the reaction vessel 12 and transmitted therethrough to the sleeve 11 as gases exert pressure against the inner cylinder 12. As used herein, the term "textile" includes fiber, filaments, yarns, and fabrics; e.g., *Hoechst Celanese Dictionary of Fiber & Textile Technology* (1990 Hoechst Celanese Corporation) at page 157. Thus, the would layers of filaments or yarns described herein are properly referred to as textile layers, as are the layers of woven, nonwoven, knitted, or braided fabric.

In order to obtain the strength advantages generally required under pressure, the composite sleeve 11 preferably further comprises at least one structural polymer layer 26 between the wound layer 24 and the outer polymer layer 25. In preferred embodiments, the structural polymer layer 26 is an engineering resin, with materials such as polyimides being most preferred. By comparison, the inner layer 23 and outer layers 25 are typically selected for chemical inertness and are often formed of polytetrafluoroethylene or some other generally inert polymeric material. Appropriate engineering resins are well known to those of ordinary skill in these arts and can be selected and manufactured without undue experimentation. Exemplary resins are described at column 6, lines 10–40 of Pat. No. 5,520,886, or in Lewis, *Hawley's Condensed Chemical Dictionary*, 12$^{th}$ Edition at pages 464–65 ("engineering material").

Figure 6:
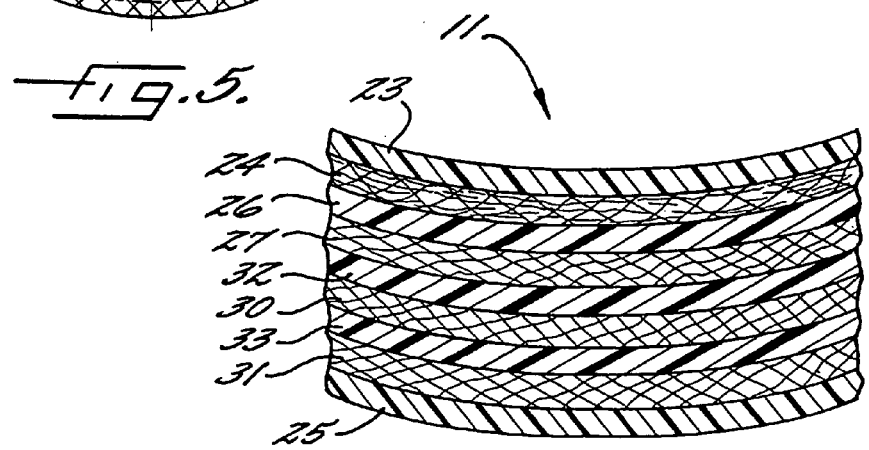
FIG. 6 is a cross-sectional view taken along lines 6—6 of FIG. 5 and illustrating the composite material used to form the sleeve.

As FIG. 6 illustrates, in the most preferred embodiments, the composite sleeve 11 further comprises a plurality of pairs of adjacent concentric layers of structural polymer and fabric in addition to the wound layer 24 and the outer polymer layer 25. FIG. 6 illustrates three additional fabric layers 27, 30, and 31 and two additional layers 32 and 33 of the preferred engineering resin.

It will be understood that the fabric layers 27, 30, and 31 can also be wound in the same manner as the layer 24, or alternatively, because of the strength advantages provided by even one wound layer, the additional fabric layers can comprise the woven, nonwoven, braided, or knitted fabrics previously used in such composite sleeves. Thus, at least one, possibly several, and potentially all of the fabric layers can be wound.

Although the illustrated embodiment shows the wound layer 24 as the innermost textile layer, it will be understood that if a single wound layer is incorporated, it can comprise the innermost textile layer, the outermost textile layer, or any one or more layers in between. Furthermore, textile layers can be positioned directly adjacent one another, including wound layers on wound layers, and (in a particularly preferred embodiment) wound layers on woven (or other fabric) layers.

The windings used to make the layer 24 are selected from the group consisting of filaments and yarns, with TEFLON®-coated fiberglass yarns being presently most preferred. Other yarns or filaments can also be used provided they have the required characteristics of microwave transparency, chemical inertness, and appropriate strength.

Accordingly, in another aspect, the invention comprises the protective composite sleeve material itself which comprises the microwave transparent wound fabric layer fixed with the microwave transparent structural medium with the wound layer being selected from the group consisting of filaments and yarns. As in the previous embodiments, the structural medium is preferably a first polymer, preferably an engineering resin such as a polyimide. The inner and outer layers are selected for chemical inertness and preferably comprise polytetrafluoroethylene. The material can include as many pairs of additional structural polymers and additional structural textile layers as may be desired or necessary with a total of four or five textile layers (including the wound layer) being most preferred.

The composite sleeve illustrated in FIGS. 5 and 6 can be formed in any manner suitable to achieve the final structure, one example of which will be described herein. In a preferred technique, TEFLON® tape is wrapped on a mandrel (preferably one of surface-hardened aluminum) having a diameter the same as the desired inner diameter of the composite sleeve. When properly wound, the TEFLON® tape forms a cylinder over the mandrel.

In a next step, the yarn or filament is wound over the TEFLON® tape under tension, and with the filaments or yarns closely adjacent one another. The yarn can be wound in single or multiple passes (i.e., to form wound-on-wound layers) depending upon the desired end structure. The yarn layer is then wound (i.e., covered) with a tape of the desired engineering resin.

Next, in presently preferred embodiments, a woven fiberglass fabric is added as a sock over the layer of engineering resin tape on the mandrel. Before being added, the fiberglass sock is heat-treated, typically using a microwave technique, to remove any carbon or other impurities that would be responsive to microwave radiation in the final composite sleeve. As noted above, the successive fabric layers could alternatively be wound rather than woven just like the first fabric layer.

Furthermore, if desired, two or more wound layers can be adjacent one another, or a wound layer can be adjacent a woven (or other fabric) layer without any polymer layer therebetween.

Additional layers of engineering resin tape and fabric or windings are added in the same manner to obtain the desired number of layers of each.

In the next-to-last step, another layer of TEFLON® tape is wound over the outermost layer of fabric. As a final winding step, a heat-shrinkable tape is wound over the outermost coating of the cylinder precursor materials on the mandrel. The mandrel and the wound and sock type layers are then heated to an appropriate temperature (325° C. for about 40 minutes in preferred embodiments) to melt the resins. At the same time the tape shrinks under the influence of heat thus applying a compressive force to the entire structure which gives it additional structural strength.

After the heating step, the mandrels and surrounding materials are allowed to cool after which the sleeves are removed from the mandrel and cut into appropriate lengths for use with the vessels described herein.

As recognized by those who use microwave assisted chemistry on a regular basis, the vessel assemblies described herein are typically, and in many cases preferably, used in systems for microwave assisted chemistry that comprise a source of microwave radiation, a cavity (resonator) in microwave communication with the source, and a plurality of the reaction vessels of the type described herein in the cavity. In many cases, the vessels are placed upon a reciprocating turntable that helps move the vessels slightly through the microwave pattern that becomes established in the cavity. Magnetrons are typically used as sources for such devices because of their availability, reliability, and cost effectiveness. Other sources such as klystrons, solid-state sources, or switching power supplies (converters or inverters) can also be incorporated as is described, for example, in co-pending and commonly assigned patent application Ser. No. 09/063, 545, filed Apr. 21, 1998, for "Use of Continuously Variable Power in Microwave Assisted Chemistry."

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A self sealing vessel assembly for high pressure microwave assisted chemistry, said vessel assembly comprising:
   a polymeric cylinder and a circular polymeric cap for said cylinder;
   said cylinder being closed at one end and open at the other end to receive said cap;
   said open end of said cylinder comprising a lip that is beveled inwardly from said open end;
   said circular polymeric cap having a beveled lower edge that engages said beveled lip when said cap is place upon said polymeric cylinder;
   a composite sleeve surrounding said polymeric cylinder, said composite sleeve being formed of a microwave transparent inner cylindrical tetrafluoroethylene polymeric layer, a first microwave transparent wound layer adjacent to and concentric with said inner polymeric layer in which said winding is selected from the group consisting of filaments and yarns, a structural polymer layer on said wound layer, and a microwave transparent outer tetrafluoroethylene polymeric layer on said structural polymer layer;
   a supporting frame that extends along said cylinder and across said lid and across said closed end of said cylinder for preventing said lid from being displaced from said cylinder when pressure is generated inside of said vessel; and
   a choke cylinder depending from said beveled lower edge of said cap, said choke cylinder having an outer diameter substantially the same as the inner diameter of said polymeric cylinder so that said choke provides a self sealing mechanism for said cylinder as pressure from a chemical reaction increases within said cylinder.

2. A vessel assembly according to claim 1 wherein said frame comprises:
   a threaded opening in said frame adjacent said cap; and
   a bolt in said threaded opening that bears on said cap when tightened in said threaded opening.

3. A vessel assembly according to claim 1 wherein said cap and said cylinder both comprise fluorinated hydrocarbons.

4. A composite sleeve according to claim 1 comprising a plurality of pairs of adjacent concentric layers of structural polymer and textiles between said first wound layer and said outer polymeric layer.

5. A composite sleeve according to claim 4 wherein said textile layers in said pairs are selected from the group consisting of woven fabrics, braided fabrics, nonwoven fabrics, and knitted fabrics.

6. A composite sleeve according to claim 4 wherein said textile layers in said pairs comprise a winding selected from the group consisting of filaments and yarns.

7. A vessel assembly according to claim 1 wherein said supporting frame is flexible under a predetermined force exerted by pressure inside said cylinder and against said cap, so that the flexing of said frame at said pressure allows said cap to disengage from said cylinder and release the pressure inside.

8. A system for microwave assisted chemistry comprising:
   a source of microwave radiation;
   a cavity in microwave communication with said source; and
   a plurality of vessels according to claim 1 in said cavity.

9. A system according to claim 8 wherein said source is selected from the group consisting of magnetrons, klystrons, solid state devices, and switching power supplies.

10. A system according to claim 8 and further comprising a waveguide between said source and said cavity.

* * * * *